US006469156B1

(12) United States Patent
Schafer et al.

(10) Patent No.: US 6,469,156 B1
(45) Date of Patent: Oct. 22, 2002

(54) **RAPID AND SENSITIVE METHOD FOR DETECTING *HISTOPLASMA CAPSULATUM***

(75) Inventors: Millie P. Schafer; Thomas M. Reid, both of Cincinnati, OH (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/673,298

(22) PCT Filed: Apr. 20, 1999

(86) PCT No.: PCT/US99/08731

§ 371 (c)(1),
(2), (4) Date: Jan. 12, 2001

(87) PCT Pub. No.: WO99/54508

PCT Pub. Date: Oct. 28, 1999

(51) Int. Cl.$^7$ .......................... C07H 21/04; C12Q 1/68; C12Q 19/34
(52) U.S. Cl. .................. 536/24.32; 536/23.1; 536/24.1; 536/24.3; 536/24.33; 435/6; 435/91.1; 435/91.2
(58) Field of Search .......................... 435/6, 91.1, 91.2; 536/24.1, 24.33

(56) References Cited

U.S. PATENT DOCUMENTS

| | | | |
|---|---|---|---|
| 4,851,330 A | 7/1989 | Kohne | 435/6 |
| 5,093,118 A | 3/1992 | Klein et al. | 424/88 |
| 5,352,579 A | 10/1994 | Milliman | 435/6 |
| 5,426,027 A | 6/1995 | Lott et al. | 435/6 |
| 5,580,971 A | 12/1996 | Mitsuhashi | 536/24.32 |
| 5,582,985 A | 12/1996 | Thompson | 435/6 |
| 5,585,238 A | 12/1996 | Ligon et al. | 435/6 |
| 5,693,501 A | 12/1997 | Lee et al. | 435/91.2 |

FOREIGN PATENT DOCUMENTS

| | | |
|---|---|---|
| WO | WO 96/19588 A2 | 6/1996 |
| WO | WO 96/21741 A | 7/1996 |

OTHER PUBLICATIONS

Kappe (GenEmbl Accession No. Y13999 (1997)).*
Berbee et al. (GenEmbl Accession No. U18363 (1995)).*
LoBuglio et al. (J. of Clin. Micro. 33(1): 85–89 (1995)).*
Mayer & Lasker. "PCR identification of Histoplasma capsulatum using a fluorogenic probe to detect amplified target DNA",96$^{th}$ *General Meeting of the American Society for Microbiology*, May 19–23, 1996.
Kreader CA. "Relief of Amplification Inhibition in PCR with Bovine Serum Albumin or T4 Gene 32 Protein," *Appl. Env. Microbiol.* 62: 1102–1106, 1996.
Sandhu et al. "Molecular Probes for Diagnosis of Fungal Infections," *J Clin. Microbiology* 33(11): 2913–2919, Nov. 1995.

Berbee et al. Histoplasma (Ajellomyces) capsulatus 5.8S rRNA gene, complete sequence, including ITS1 and ITS2. GeneBank Accession No.: U18363, 1994.
Berbee et al. "Blastomyces (Ajellomyces) dermatitidis 5.8S rRNA gene, complete sequence, including ITS1 and ITS2," GeneBank Accession No.; U18364, 1994.
Berbee et al. "Is Penicillium monophyletic? An evaluation of phylogeny in the family Trichocomaceae from 18S, 5.8S and ITS ribosomal DNA sequence data," *Submitted EMBL/GenBank/DDBJ databases* Dec. 10, 1994.
Mitchell et al. "Unique Oligonucleotide Primers in PCR for Identification of *Cryptococcus neoformans,*" *J Clin Microbiology* 32(1): 253–255, Jan. 1994.
Hall G.S. "Probe Technology for the Clinical Microbiology Laboratory," *Arch Pathol. Lab. Med.* 117: 578–583, Jun. 1993.
Stockman et al. "Evaluation of Commercially Available Acridinium Ester–Labeled Chemiluminescent DNA Probes for Culture Identification of *Blastomyces dermatitidis, Coccidiodes immitis, Cryptococcus neoformans,* and *Histoplasma capsultaum,*" *J Clin. Microbiology* 31(4): 845–850, Apr. 1993.
Woods et al. "Fast DNA Isolation from *Histoplasma capsulatum*: Methodology for Arbitrary Primer Polymerase Chain Reaction–Based Epidemiological and Clinical Studies," *J Clin. Microbiology* 31(2): 463–464, Feb. 1993.
Padhye et al. "Comparative Evaluation of a Chemiluminescent DNA Probe and Exoantigen Test for Rapid Identification of *Histoplasma capsulatum,*" *J Clin. Microbiology* 30(12): 3108–3111, Dec. 1992.
Keath et al. "Typing of *Histoplasma capsulatum* by Restriction Fragment Length Polymorphisms in a Nuclear Gene," *J Clin. Microbiology* 30(8): 2104–2107, Aug. 1992.
White et al. "Amplification and Direct Sequencing of Fungal Ribosomal RNA Genes for Phylogenetics," *PCR Protocols: A Guide to Methods and Applications,* Academic Press, pp. 315–322, 1990.
Tsai and Olson. "Rapid Method for Separation of Bacterial DNA from Humic Substances in Sediments for Polymerase Chain Reaction," *Appl. Env. Microbiol.* 58: 2292–2295, 1992.
Schafer MP. "Moleclular Cloning and Sequence Analysis of the H+ATPase Gene from the Human Dimorphic Pathogen *Histoplasma capsultaum,*" Ph.D. Thesis, University of Cincinnati, 1991.

(List continued on next page.)

Primary Examiner—Kenneth R. Horlick
Assistant Examiner—Alexander H. Spiegler
(74) Attorney, Agent, or Firm—Needle & Rosenberg, P.C.

(57) ABSTRACT

Oligonucleotides are provided which are useful as primers to initiate the amplification of a segment of *Histoplasma capsulatum* DNA that is specific to *H. capsulatum,* using the polymerase chain reaction. A method of detecting the presence of *H. capsulatum* in a sample using a nested, or two-stage, PCR assay is also provided. The outer pair of primers, for use in the first stage of the assay, are fungal-specific oligonucleotides; the inner pair of primers, for use in the second stage, are oligonucleotides specific for *H. capsulatum.*

18 Claims, 2 Drawing Sheets

OTHER PUBLICATIONS

Kersulyte et al. "Diversity among Clinical Isolates of *Histoplasma capsulatum* Detected by Polymerase Chain Reaction with Arbitrary Primers," *J Bacteriology* 174(22): 7075–7079, Nov. 1992.

Spitzer et al. "Use of Mitochondrial and Ribosomal DNA Polymorphisms to Classify Clinical and Soil Isolates of *Histoplasma capsulatum*," *Infection and Immunity* 57(5): 1409–1412, May 1989.

Gaur, et al. "Preliminary visual screening of soil samples for the presumptive presence of *Histoplasma capsulatum*," *Mycologia* 72(2): 259–269, 1980.

van Belkum et al. "Polymerase Chain Reaction–Mediated Genotyping in Microbial Epidemiology," *Clin. Infect. Dis.* 18; 1017–1018, Jun. 1994.

Arbeit et al. "Reply," *Clin. Infect. Dis.* 18; 1018–1019, Jun. 1994.

* cited by examiner

| Lane | 1 | 2 | 3 | 4 | 5 | 6 |
|------|---|---|---|---|---|---|
| Soil | − | + | + | + | − | − |
| BSA  | − | + | + | − | + | − |
| G50  | − | − | + | + | + | + |

Soil Spiked with *H. capsulatum* Spores

Environmental Soil Samples 1 2 3 4 5 6

SEQUENCE LISTING

```
<160> NUMBER OF SEQ ID NOS: 4

<210> SEQ ID NO 1
<211> LENGTH: 19
<212> TYPE: DNA
<213> ORGANISM: UNKNOWN
<220> FEATURE:
<223> OTHER INFORMATION: PRIMER

<400> SEQUENCE: 1
tccgtaggtg aacctgcgg                                                   19

<210> SEQ ID NO 2
<211> LENGTH: 20
<212> TYPE: DNA
<213> ORGANISM: UNKNOWN
<220> FEATURE:
<223> OTHER INFORMATION: PRIMER

<400> SEQUENCE: 2
tcctccgctt attgatatgc                                                  20

<210> SEQ ID NO 3
<211> LENGTH: 18
<212> TYPE: DNA
<213> ORGANISM: UNKNOWN
<220> FEATURE:
<223> OTHER INFORMATION: PRIMER

<400> SEQUENCE: 3
ggagcctctg accgggac                                                    18

<210> SEQ ID NO 4
<211> LENGTH: 18
<212> TYPE: DNA
<213> ORGANISM: UNKNOWN
<220> FEATURE:
<223> OTHER INFORMATION: PRIMER

<400> SEQUENCE: 4
gcacgtccca ccggtcag                                                    18
```

RAPID AND SENSITIVE METHOD FOR DETECTING *HISTOPLASMA CAPSULATUM*

The present application is a 35 U.S.C. § 371 national phase application from, and claims priority to, international application PCT/US99/08731, filed Apr. 20, 1999, which claims priority to U.S. provisional patent application Ser. No. 60/082,477, filed Apr. 21, 1998, which applications are hereby incorporated herein their entirety.

FIELD OF THE INVENTION

This invention relates to detecting a pathogenic fungus, *Histoplasma capsulatum*, using oligonucleotide probes specific for *H. capsulatum* to amplify *H. capsulatum* DNA by means of the polymerase chain reaction. Test samples may originate from the environment, where *H. capsulatum* spores are found, or from clinical samples obtained from patients.

BACKGROUND OF THE INVENTION

*Histoplasma capsulatum* is a dimorphic fungus that is pathogenic in humans. In one form, the fungus has the mycelia characteristic of molds, and produces spores as an aspect of its reproduction. This form is commonly found in the ambient environment, and is highly prevalent in soils containing guano from bats or birds. In general it proliferates in soils rich in nutrients such as those containing rotting organic residues. Its morphology includes multicellular filaments containing cylindrical structures (i.e., the hyphae or conidia). This form may further contain macroconidia and microconidia which may grow in soil or on media designed for fungal growth at 25° C.

In its second form, *H. capsulatum* adopts a single celled state characteristic of yeast, and reproduces by budding. This form is prevalent on suitable nutrient media in the laboratory, and is the form generally found after it infects a human. Infection may occur upon breathing dust containing fragments of *H. capsulatum* hyphae or conidia; as noted above, such fragments may be prevalent if dust is stirred up from soil containing the droppings from birds or bats or soil that is otherwise rich in organic nutrients, especially nitrogenous nutrients.

The infection produces a systemic fungal disease, histoplasmosis, which can initially result in a variety of symptoms often dependent on the type of infection, the general health of the host, and the exposure level. In acute self-limiting infections, especially those occurring in healthy individuals, the symptoms may be very mild, such as those of a flu-like respiratory illness, with symptoms such as general malaise, fever, chest pain, a dry cough, headache, loss of appetite, shortness of breath, joint and muscle pains and chills. The severity of the symptoms may depend on how many spores have been inhaled, and the general health of the subject.

The symptoms of respiratory infection are often suppressed by the immune response. This response includes endocytosis by pulmonary macrophages. *H. capsulatum* may then proliferate within macrophages and be transported systemically as a result. As a result, such suppression appears to result in long term latency rather than in elimination of the organism. *H. capsulatum* infection can also result in calcified deposits within the lungs, produced when growth of the yeast is inhibited by host immune responses. Both the infected macrophages and the calcified deposits serve as a reservoir of latent infection. As a consequence, if the individual subsequently becomes immune compromised or immune deficient, histoplasmosis can reappear. Thus individuals such as those receiving immune-suppressing therapy, the very young or the elderly, those suffering from cancer, or expressing the symptoms of acquired immune deficiency syndrome are susceptible to recrudescence of histoplasmosis as a chronic and/or a disseminated infection, and may include ocular infection. Resurgence of such latent histoplasmosis produces potentially lethal symptoms.

Assay for *H. capsulatum* infection or its presence in a sample is carried out by methods such as culturing, immunoassay for surface antigens, and a bioassay. Currently, histoplasmosis may be diagnosed by culture, or by the demonstration of a rise in complement-fixing antibody titers in serum. A definitive diagnosis of an *H. capsulatum* infection requires the isolation and propagation of the fungus, which is time-consuming and lacks sensitivity. It is also dangerous for laboratory personnel, who must take extreme caution to prevent inhalation of the pathogenic fungus, so as not to become ill with a pulmonary infection. Further, only small quantities of antigens of *H. capsulatum* for use as biological reagents may be prepared in this manner.

Conventional laboratory identification methods used to isolate and identify *H. capsulatum* include the culture of a clinical specimen at room temperature on specialized fungal media. This procedure isolates the slower growing *H. capsulatum* colonies from possible contaminants, such as bacteria, and from faster growing saprobic fungi. This method, however, has several disadvantages. Because the growth of *H. capsulatum* to a visible colony normally takes from about two to four weeks, and sometimes as long as 12 weeks, this identification procedure is very slow. (See, for example, Rippon, *Histoplasmosis*. In *Medical Mycology, The Pathogenic Fungi and the Pathogenic Actinomyestes*, 3rd Ed., Saunders, Ch. 15 (1988); Koneman at al., *Laboratory Identification of Molds*, in *Practical Laboratory Mycology*, (3rd ed. Williams & Wilkins (1985)); and McGinnis, *Histoplasma capsulatum*, in *Laboratory Handbook of Medical Mycology*, Academic Press (1986).) Further, additional growth is required before the characteristic colony morphology and microscopic sporulation pattern with tuberculate macroconidia may be observed. In addition, approximately 10% of cultures produce only smooth-walled macroconidia, and some cultures fail to sporulate. Moreover, many species of fungi other than *H. capsulatum*, such as *Blastomyces dermatitides*, Chryacsporium sp., and Sepedonium sp., produce similar colony and sporulation characteristics. Thus, additional testing is usually necessary to definitively identify the organism.

One method of converting the mycelial colony of *H. capsulatum* to the yeast phase is performed by subculturing the organism onto highly enriched cysteine-containing media, and incubating it at 35–37° C. However, conversion to the yeast phase is often difficult, and may require several additional subcultures at three-day intervals.

Histoplasmin, an unpurified culture supernatant obtained from the mycelial phase of *H. capsulatum* contains *H. capsulatum* M antigens. Histoplasmin is currently used to probe both humoral and cell-mediated responses in patients with histoplasmosis. It is used for the serologic diagnosis of histoplasmosis, and as a skin test antigen to demonstrate delayed hypersensitivity to infection in skin tests for histoplasmosis. The purification of histoplasmin is described by Bradley et al., Infect. Immun. 9:870–880 (1974). The preparation of H and M antigens of *H. capsulatum* free of heterologous antigens is described by Green et al., Curr. Microbiol. 12:209–216 (1985). (See also, Pine, Contrib. Microbiol. Immunol. 3:138–168 (1977).) The preparation of antisera to the M antigen is described by Green et al., Infect.

Immun. 14:826–831 (1976). General information concerning the serodiagnosis of fungal diseases is present in Kaufman et al., Serodiagnosis of Fungal Diseases, in *Manual of Clinical Laboratory Immunology* (3rd ed., American Society for Microbiology, Washington, D.C.(1988)).

Serologic evidence is a principal diagnostic indicator of histoplasmosis. Several serologic tests, such as the immunodiffusion test, detect precipitants against the species-specific H and M antigens found in histoplasmin. (See, for example, Kaufman, Clin. Infect. Dis. 14:23–29 (1992), and Wheat, Eur. J. Clin. Microbiol. Infect. Dis. 8:480 (1989).)

Although the M antigen of *H. capsulatum* is useful in immunoassays for the diagnosis of histoplasmosis, purification of the M antigen from a batch culture is a laborious and low-yield process. The use of a recombinantly-produced M antigen of *H. capsulatum* in such immunoassays would significantly diminish the labor necessary to obtain M antigens which are pure enough to be useful in the immunoassays, and would result in high yields of the M antigen.

Assay for *H. capsulatum* infection historically has been via immunoassay for surface antigens. Additionally, a widely practiced assay is the mouse inoculum/agar plate culture method. This method, which involves indirect detection, takes as long as 6–8 weeks and is expensive. The method entails extracting a soil sample suspected of harboring *H. capsulatum* and injecting the extract intraperitoneally into mice. After six weeks the mice are sacrificed, and extracts of the livers and spleens are inoculated onto Sabouraud's dextrose agar. These are incubated and observed weekly for fungal growth. Any fungi resulting are then subcultured for a more definitive identification. (Ajello, L. and Weeks, R. J., in Occupational Mycoses, A Text, edited by A. F. DiSalvo, Leas & Febiger, Philadelphia, pp.229–238, 1983; Ajello, L. and Runyon, L. C., J. Bacteriol. 66:34–40, 1953). More recently molecular biological assay techniques have been developed, such as restriction fragment length polymorphism (RFLP).

U.S. Pat. No. 5,580,971 to Mitsuhashi discloses methods for detecting a particular fungus in a biological sample based on polynucleotide capture probes. In one method, the probe is complementary to a sequence in the ribosomal RNA of a particular fungus, and binding of the analyte nucleic acid is detected with a second probe whose sequence is common to a wide range of fungi. In another method, two probes are used and nucleic acid is amplified using, preferably, a polymerase whose activity is not hindered at high temperature. Many species and genera of pathogenic fungi are detectable, but *H. capsulatum* is not included in the disclosed group of fungi.

WO 96 19588 discloses a nucleic acid hybridization probe derived from the saccharopine dehydrogenase of Candida albicans that is conserved in fungi. The probe, and an assay method employing the probe, may be used for detection of a variety of fungi from different genera. WO 96 21741 discloses oligonucleotide probes considered to be universal primers for 28S rRNA of fungi. An extensive range of species and genera of fungi is disclosed as being detectable by amplification methods using the probes, including *H. capsulatum*.

Padhye et al. (J. Clin. Microbiol. 30, 3108–3111 (1992)) describe application of the Accuprobe™ (Gen Probe, Inc., San Diego, Calif.) assay for *H. capsulatum*. Accuprobe is a DNA-based probe in which hybridization between the probe and RNA from the organism is detected by a chemiluminescent assay. 103 of 105 *H. capsulatum* samples were identified by the assay, with assay times of about 2 hrs. Hall (Arch. Pathol. Lab. Med. 117, 578–583 (1993)) reviews applications of the Accuprobe™ assay in general, and summarizes the organisms for which Accuprobes™ were available. *H. capsulatum* is included among these. Hall does not provide the structure of the *H. capsulatum* probe.

Spitzer et al. (Infect. Immun. 57, 1409–1412 (1989)) disclose classification of ambient and clinical isolates of *H. capsulatum* based on analysis of mitochondrial DNA and ribosomal DNA. Keath et al. (J. Clin. Microbiol. 30, 2104–2107 (1992)) present analyses of a large number of clinical and soil samples of *H. capsulatum* using restriction fragment length polymorphisms (RFLP). The nuclear gene probe yps-3 and a mitochondrial DNA probe were employed, and permitted classification into the known, as well as the identification of new, classes and subclasses of the fungus.

Kersulyte et al. (J. Bact. 174, 7075–7079 (1992)) show that a polymerase chain reaction-based amplification based on random primers drawn from the fungal genome, and RFLP analysis resolves various isolates of *H. capsulatum* into a range of strains. They find that *H. capsulatum* is an extremely diverse species. Woods et al. (J. Clin. Microbiol. 31, 463–464 (1993)) teach that use of randomly chosen primers for use in the polymerase chain reaction allows simple and rapid detection of variant isolates of *H. capsulatum*. They describe a rapid isolation method to obtain DNA from *H. capsulatum* in order to permit sensitive identification of *H. capsulatum* strains.

U.S. Pat. No. 5,352,579 to Milliman discloses probes for the detection of *Histoplasma capsulatum* which distinguishes between *H. capsulatum* and its known closest phylogenetically related organisms. The invention is based on a hybridization probe capable of effecting this distinction. The probe is complementary to a variable region of rRNA or rDNA. A method of assaying for *H. capsulatum* using this probe is also provided. Mayer et al. (96th General Meeting, Amer. Soc. for Microbiol., New Orleans, La., May 19–23, 1996) have devised a set of PCR probes (whose sequences were not disclosed) that are complementary to the gene for the H antigen of *H. capsulatum* var. *capsulatum* and var. *duboisii* that amplifies *H. capsulatum* DNA with specificity and sensitivity. They also disclose the use of a nucleotide probe in a TaqMan assay, wherein the probe hybridizes to a region of *H. capsulatum* between the binding sites of two PCR probes. In the assay Taq polymerase liberates a luminescent probe from a quenching environment if the probe binds target DNA.

Presently, the method used to isolate and identify *H. capsulatum* is expensive and requires several weeks to complete. The expense is increased by the number of samples required. If not enough samples are collected, small but highly contaminated areas can be overlooked. See, e.g., "Histoplasmosis: Protecting Workers at Risk", Dept. of Health and Human Services Publication No. 97–146, September 1997. Therefore, in the current status of the field, there remains a need for a specific, sensitive, and rapid assay for *H. capsulatum*, both in environmental samples and in clinical samples from patients suspected of harboring *H. capsulatum* infection. The present invention provides such methods and assays.

SUMMARY OF THE INVENTION

The present invention provides oligonucleotides which are useful as primers to initiate the amplification of a segment of *H. capsulatum* DNA that is specific to *H.*

*capsulatum* using the polymerase chain reaction. The present invention also provides methods of detecting the presence of *H. capsulatum* in a sample using a nested, or two-stage, PCR assay.

The invention discloses an oligonucleotide primer pair including sequences specific for the 5.8S rRNA gene of *Histoplasma capsulatum*, to be used in the second stage of the PCR assay, or an oligonucleotide primer pair, each of which includes a sequence complementary to one or the other of the primer pair specific for the *H. capsulatum* 5.8S rRNA gene. In a significant embodiment, the oligonucleotide primer pair is disclosed as an oligonucleotide containing the sequence given by SEQ ID NO:3, and an oligonucleotide containing the sequence given by SEQ ID NO:4. The invention additionally discloses an oligonucleotide containing a sequence complementary to that given in SEQ ID NO:3, and an oligonucleotide containing a sequence complementary to that given in SEQ ID NO: 4. These complementary oligonucleotides are useful to prepare the actual PCR primers of the invention by the action of a DNA polymerase, and in probing test samples for the presence of *H. capsulatum* DNA.

The methods of the invention detect the presence of *Histoplasma capsulatum* in a sample. One of these methods includes the steps of:

(a) providing a sample suspected of harboring *H. capsulatum*;

(b) preparing a first amplified nucleic acid by contacting the sample with a first solution comprising an oligonucleotide primer pair specific for a fungal nucleic acid sequence that comprises the coding sequence for the 5.8S rRNA gene, a first DNA polymerase, and a first mixture of deoxynucleotide triphosphates, in a first buffer, and carrying out a polymerase chain reaction on the first solution resulting therefrom;

(c) preparing a second amplified nucleic acid by contacting all or a portion of the first amplified nucleic acid from step (b) with a second solution comprising an oligonucleotide primer pair specific for the *H. capsulatum* 5.8S rRNA gene, a second DNA polymerase, and a second mixture of deoxynucleotide triphosphates, in a second buffer, and carrying out a polymerase chain reaction on the second solution resulting therefrom; and (d) detecting the presence of DNA derived from *H. capsulatum* in the second amplified nucleic acid, whereby the presence of DNA derived from *H. capsulatum* in the second amplified nucleic acid indicates that *H. capsulatum* occurs in the sample. In a preferred embodiment of the above method, the oligonucleotide primer pair employed in step (b) is specific for the fungal internal transcribed spacer (ITS) regions flanking the coding sequence for the 5.8S rRNA gene (see FIG. 1).

The invention additionally provides a method of detecting the presence of *Histoplasma capsulatum* in a sample, including (a) providing a sample suspected of harboring *H. capsulatum*;

(b) preparing a first amplified nucleic acid by contacting the sample with a first solution comprising an oligonucleotide comprising the sequence given by SEQ ID NO:1, an oligonucleotide comprising the sequence given by SEQ ID NO:2, a first DNA polymerase, and a first mixture of deoxynucleoside triphosphates, in a first buffer, and carrying out a polymerase chain reaction on the first solution resulting therefrom;

(c) preparing a second amplified nucleic acid by contacting all or a portion of the first amplified nucleic acid from step (b) with a second solution comprising an oligonucleotide comprising the sequence given by SEQ ID NO:3, an oligonucleotide comprising the sequence given by SEQ ID NO:4, a second DNA polymerase, and a second mixture of deoxynucleoside triphosphates, in a second buffer, and carrying out a polymerase chain reaction on the second solution resulting therefrom; and (d) detecting the presence of DNA derived from *H. capsulatum* in the second amplified nucleic acid, whereby the presence of DNA derived from *H. capsulatum* in the second amplified nucleic acid indicates that *H. capsulatum* occurs in the sample.

In preferred embodiments of the methods of the invention the samples can be environmental samples, including soil samples, or clinical samples from human subjects. Furthermore, in a preferred embodiment of the methods of the invention, the partial purification step includes separating any soil contained in the sample from the *H. capsulatum* nucleic acid. In still another preferred embodiment of the invention, the first buffer contains bovine serum albumin. In additional preferred embodiments of the methods the detecting step includes gel electrophoresis of the second amplified nucleic acid and detecting any *H. capsulatum*-specific DNA in the resulting gel, or contacting the second amplified nucleic acid with a labeled probe specific to *H. capsulatum*-specific DNA and detecting the label.

BRIEF DESCRIPTION OF THE DRAWING

FIG. 3. Effect of including bovine serum albumin as a buffer component, and gel filtration as a step, on inhibition of PCR amplification by soil. Lane 1, 10 ng *H. capsulatum* DNA; Lane 2, 10 ng *H. capsulatum* DNA, untreated soil, and bovine serum albumin (BSA); Lane 3, 10 ng *H. capsulatum* DNA, BSA, and soil that had been treated with a Sephadex G-50 spin column; Lane 4, 10 ng *H. capsulatum* DNA and soil that had been treated with a Sephadex G-50 spin column; Lane 5, 10 ng *H. capsulatum* DNA, BSA, and treatment with a Sephadex G-50 spin column; Lane 6, 10 ng *H. capsulatum* DNA, and treatment with a Sephadex G-50 spin column.

FIG. 4. Detection of *H. capsulatum* DNA in soil samples using two-stage PCR. Panel A: Detection of *H. capsulatum* by PCR in soil spiked with *H. capsulatum* spores. Lane 1, 10 pg *H. capsulatum* DNA; Lane 2, 10 *H. capsulatum* spores; Lane 3, Soil that is free of *H. capsulatum* spiked with 1,000 *H. capsulatum* spores; Lane 4, Soil that is free of *H. capsulatum* spiked with 500 *H. capsulatum* spores; Lane 5, Soil that is free of *H. capsulatum*; Lane 6, 100 bp ladder of DNA markers. Panel B: Detection of *H. capsulatum* by PCR in soil known to contain *H. capsulatum*. Lane 1, 1 pg *H.*

Figure 1:
FIG. 1. Schematic diagram of fungal ribosomal RNA genes.
Figure 2:
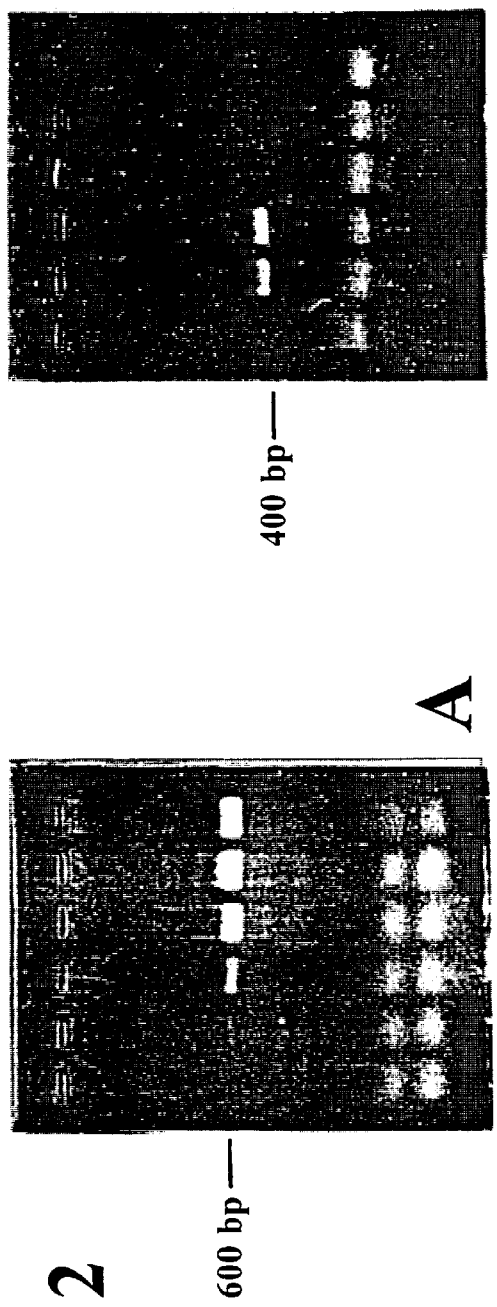
FIG. 2. Sensitivity and specificity of two-stage PCR for *H. capsulatum* DNA. Panel A: Gel electrophoretogram showing results of first PCR stage based on fungal-specific primers. Lane 1, 50 fg *H. capsulatum* DNA; Lane 2, 100 fg *H. capsulatum* DNA; Lane 3, 1,000 fg *H. capsulatum* DNA; Lane 4, 25 ng *Blastomyces dermatitidis* DNA; Lane 5, 50 ng *B. dermatitidis* DNA; Lane 6, 100 ng *B. dermatitidis* DNA. Panel B: Gel electrophoretogram showing results of second PCR stage based on *H. capsulatum*-specific primers. Lane 7, 50 fg *H. capsulatum* DNA; Lane 8, 100 fg *H. capsulatum* DNA; Lane 9, 1,000 fg *H. capsulatum* DNA; Lane 10, 25 ng *B. dermatitidis* DNA; Lane 11, 50 ng *B. dermatitidis* DNA; Lane 12, 100 ng *B. dermatitidis* DNA.

*capsulatum* DNA; Lane 2, contaminated soil, sample "HC-13"; Lane 3, contaminated soil, sample "HC-14"; Lane 4, contaminated soil, sample "HC-14"; Lane 5, 10 *H. capsulatum* spores; Lane 6, negative control.

DETAILED DESCRIPTION OF THE INVENTION

As used herein the terms "specific to" or "specific for" a target sequence, in relation to a nucleic acid sequence such as an oligonucleotide sequence, relate to a nucleotide sequence that hybridizes, under conditions used in given experimental circumstances, to the target but does not hybridize under those circumstances to sequences that are not target sequence. Nucleotide sequences that are included in the subject matter of the present invention, are those that include bases every one of which is complementary to the corresponding base on the target. The target nucleic acid sequences envisioned in this invention include those that occur in all subspecies and strains of *H. capsulatum* currently known, and in equivalent subspecies and strains of *H. capsulatum* that may remain to be discovered. The nucleic acids and oligonucleotides of the invention, therefore, include all those molecules fully complementary to target sequences occurring in any subspecies or strain of *H. capsulatum*.

As used herein, in addition, "specificity" of a nucleic acid sequence for a target sequence also encompasses nucleic acids and oligonucleotides a small number of whose nucleotides may not be complementary to the corresponding nucleotide of the target sequence. Such sequences are still "specific" for the target sequence, as used herein, as long as, the extent of deviation from complementarity remains functionally of no consequence. In particular, such a sequence is "specific" for the target sequence as long as it hybridizes effectively to the target sequence but does not hybridize to any sequence that is not a target sequence, under the conditions used in given experimental circumstances.

As used herein the term "polymerase chain reaction (PCR)" relates to a procedure whereby a limited segment of a nucleic acid molecule, which frequently is a desired or targeted segment, is amplified repetitively to produce a large amount of DNA molecules which consist only of the segment. The procedure depends on repetition of a large number of replication cycles. In each cycle, two oligonucleotide primers bind to the segment, and define the limits of the segment. A primer-dependent DNA polymerase then transcribes, or replicates, the strands to which the primers have bound. Thus in each cycle, the number of DNA duplexes is doubled.

As used herein the term "primer" or "oligonucleotide primer" relates to an oligonucleotide having a specific or desired nucleotide sequence which is complementary to a particular sequence on one of the strands of a DNA duplex. When the primer is caused to hybridize to the specific sequence in a DNA duplex to which it is complementary, it may serve as the priming position, or the initiation position, for the action of a primer-dependent DNA polymerase activity. The primer, once hybridized, acts to define one end of the operation of the replication activity of the polymerase on the duplex. A specific pair of primers is employed, wherein each hybridizes to one of the strands such that transcription, which proceeds from 5' to 3', is in the direction leading to the site of hybridization of the second primer to the opposite strand of the duplex. After several rounds of hybridization and transcription, the amplified DNA produced is a segment having a defined length whose ends are defined by the sites to which the primers hybridize.

PCR is well known to skilled artisans in the fields of molecular biology and genetic engineering, and is described in general terms and with operational detail in, for example, "Current Protocols in Molecular Biology", Ausubel et al., John Wiley and Sons, New York 1987 (updated quarterly); "Molecular Cloning: A Laboratory Manual", 2nd Ed., Sambrook, Fritsch and Maniatis, Cold Spring Harbor Laboratory, Cold Spring Harbor, N.Y., 1989; "PCR Protocols: A Guide to Methods and Applications", Innis et al., Academic Press, NY 1990; and U.S. Pat. No. 4,965,188, issued Oct. 23, 1990 to Mullis et al.; all of which are incorporated herein by reference in their entirety.

The oligonucleotide primers of the invention are intended for use in a PCR-based amplification of a target segment of DNA from *H. capsulatum*. PCR relies on the action of a DNA polymerase such as Taq polymerase, to replicate the DNA segment beyond the 3' termini of the primers. Each primer may consist only of the nucleotides given by SEQ ID NOs: 1–4, respectively. Alternatively, any primer may also contain additional sequences. If so, the hybridizing sequences in the primer pair that specifically hybridize to the target nucleic acid, such as those given by SEQ ID NOs: 1–4 must not be interrupted by any additional nucleotides. Since polymerases extend a chain in the direction from 5' to 3', the specific hybridizing sequences, such as the sequences given by SEQ ID NOs: 1–4, must appear at the 3' end of any primer containing additional nucleotides.

Additionally oligonucleotides that include the complements of the primer sequence that hybridize to the target nucleic acid, such as the complements to the sequences given by SEQ ID NOs:1–4, are also disclosed in the invention. These may consist only of the respective complementary sequences, or they may contain additional sequences with the proviso that the respective complementary sequences are intact and not interrupted by any inserted nucleotides. Such complementary oligonucleotides may be employed as probes for *H. capsulatum* DNA. They may also be used to prepare the PCR primers of the invention by means of a DNA polymerase. For such purposes the complementary sequence must appear at the 5' end of the molecule such that action of the polymerase will generate a primer oligonucleotide having its complementary sequence at its 3' end, as required according to the discussion in the preceding paragraph.

A wide variety of samples suspected of harboring *H. capsulatum* may be analyzed by the methods of the present invention. For example, in order to protect the public health, the invention envisions assaying environmental samples containing soil for the presence of the pathogen. As used herein, the term "soil" is intended broadly to include any portion of earth, soil, dust, or naturally occurring powders, as well as soils that include decaying vegetation, soils that include decaying feces from birds and bats, and the like. Since it is known that spores of *H. capsulatum* occur with relatively high prevalence in decaying deposits of feces from birds or bats, it is to be understood that significant locations from which samples may be drawn include places where these deposits are prevalent, such as chicken or poultry coops, sheds, and yards; barns; caves; and the like.

Additionally, clinical samples drawn from human subjects may be analyzed by the methods of the present invention. Candidate subjects from whom samples may be obtained are those suspected of having contracted fresh histoplasmosis as a result of symptomology. Persons exhibiting symptoms such as mild malaise and flu-like illness may be suspected of suffering from newly contracted histoplasmosis. In addition, an important group of candidate subjects includes those who may be immune compromised, such as the very young, the very old, those receiving immunosuppressive pharmacotherapy, those suffering from cancer, and those suffering from immune suppressing diseases such as acquired immune deficiency disease. Such individuals are susceptible to a recrudescence of histoplasmosis from a latent infection. Latency may have originated from earlier endocytosis of *H. capsulatum* by pulmonary macrophages, or from the calcified deposits within the lungs, produced when growth of the yeast form is inhibited by host immune responses. In such individuals, chronic or disseminated forms of the disease could occur. Chronic pulmonary histoplasmosis leads to symptoms that are similar to those of tuberculosis, and last for many months. Disseminated infections produce symptoms usually involving chronic fever, weight loss, and so forth. In addition, ocular histoplasmosis may lead to visual loss including blindness. Symptoms such as those described here would lead to a suspicion of recurring histoplasmosis in these patients. As described above, either macrophages or calcified deposits, or other sources within the body may serve as a reservoir of latent infection for extended periods of time.

Samples from candidate subjects may be drawn from several sources, including by way of nonlimiting example, blood or any other body fluids, and importantly in the methods of the invention, those fluids in which macrophages that could harbor *H. capsulatum* are found, biopsies from any tissues of the body, including lung calcifications or other locations where *H. capsulatum* infection is suspected, and the like.

In order to practice the method of the invention, a sample suspected of harboring *H. capsulatum* is obtained. A sample originating from an environmental soil sample is generally understood to include *H. capsulatum* spores. The sample is concentrated and subjected to a procedure that may partially purify *H. capsulatum* nucleic acids compared to the state of the sample as provided. The spores are then inactivated by heat treatment, such as exposure to temperatures in the range of about 60° C. to about 70° C., preferably about 65° C., for times ranging from about 30 min to about 2 hrs., preferably about 60 min. The samples are then subjected to a process that separates the samples from much of the remaining matter in the soil sample, including inorganic mineral particles and organic matter that may be present. Such partial purification, for example, may be achieved by placing the sample on top of a gel permeation medium such as, for example, Sephadex™ (Pharmacia Biotech, Piscataway, N.J.) and centrifuged, whereupon the spores and/or the fungal DNA collect in the permeate (Tsai, Y. L., and Olson, B. H., Appl. Envir. Microbiol. 58, 2292–2295 (1992)). Since soil may be inhibitory to the PCR process, it is generally preferred that such a partial purification be carried out on such samples.

Clinical samples may include *H. capsulatum* either in the spore or yeast form. Clinical samples may be concentrated and partially purified by procedures similar to those applied with soil samples.

Fungal DNA is released from fungal cells thus becoming available for the PCR amplification reaction. Without wishing to be limited by theory, it is believed that the preliminary heat treatment described above, as well as the heating that occurs in the first step of the PCR process, described further below (see Example 1), disrupts the *H. capsulatum* cells and liberates the nucleic acids. Of course, other methods of liberating the nucleic acids may be used if desired.

The sample suspected of harboring *H. capsulatum* nucleic acids is then subjected to a two-stage nested PCR amplification. Nested PCR significantly enhances both the specificity and the sensitivity of the assay, since more than one pair of primers is used in sequential PCR reactions. The DNA segment selected by the second primer pair must reside within the segment produced by the first primer pair. In the first PCR stage, a portion or all of the sample is contacted with a first pair of primers and a first DNA polymerase. These primers are an oligonucleotide primer pair specific for a fungal nucleic acid sequence that includes the coding sequence for the 5.8S rRNA gene. In a preferred embodiment of the invention, the oligonucleotides of the first primer pair are specific for the internal transcribed spacer (ITS) regions flanking the gene for 5.8S ribosomal RNA in a broad range of fungal species, shown in FIG. 1. In a particular embodiment of the invention provided in the Examples, an ITS oligonucleotide containing the sequence given by SEQ ID NO:1 (ITS-1 in FIG. 1), and an ITS oligonucleotide containing the sequence given by SEQ ID NO:2 (ITS-4 in FIG. 1), are employed (White, J., PCR Protocols: A guide to Methods and Applications, Academic Press, 1990, pp. 315–322). This primer pair is specific for most fungi, and yields PCR products of approximately 600 to 650 bp (Taylor, J., J. Clin. Microbiol. 32, 255–255 (199+)). Important genera of fungus detected include Cryptococcus, Candida strains as well as Histoplasma and Blastomyces.

As noted above, the test sample may contain further substances that have an inhibitory effect on the PCR process. Samples originating from soil, for example, may contain soluble components, such as humic acid, that interfere with the method. Accordingly, appropriate components must be introduced that neutralize any potential inhibitors or interfering substances. One additive found to be effective in the method of the present invention is bovine serum albumin (BSA) (Kreader, C. A., Appl. Envir. Microbiol. 62, 1102–1106 (1996)); this protein is included as a component of the buffer for the first stage of PCR in a significant embodiment of the invention.

PCR amplification is then conducted on the resulting mixture using a temperature program and for a number of thermal cycles sufficient to amplify the target DNA, if present. An example of a temperature program is an initial heating step at a high temperature (about 85 to about 99° C.) for a short time, followed by cycles of melting at a similar high temperature (about 85 to about 99° C.), hybridization of the PCR probes at a low temperature (about 40 to about 65° C.), and synthesis of new DNA strands at a moderate temperature (about 65 to about 80° C.). The number of thermal cycles may generally range from about 20 to about 40 or more. Advantageously a larger number of cycles is used rather than a smaller number. The PCR reaction is conveniently carried out in any PCR thermal cycling apparatus available commercially, such as those manufactured by Perkin Elmer Applied Biosystems, Foster City, Calif., or Qiagen, Chatsworth, Calif. The amplified DNA that results from the first PCR stage is a segment of DNA from *H. capsulatum* and related fungi. Omission of this first PCR stage was found to diminish the sensitivity and specificity of the method.

In the second PCR stage, a portion or all of the sample is contacted with a second pair of primers and a second DNA polymerase. The second pair of primers contains sequences found within the DNA fragment that is the product of the first stage of amplification, and that are specific for the sequence coding for the *H. capsulatum* 5.8S rRNA gene (see FIG. 1). In a preferred embodiment of the invention, an oligonucleotide containing the sequence given by SEQ ID NO:3 (HC-1 in FIG. 1), and an oligonucleotide containing the sequence given by SEQ ID NO:4 (HC-2 in FIG. 1). PCR amplification is then conducted on the resulting mixture a second time, using similar procedures as with the first stage. The buffer used in the second stage may or may not contain BSA. This stage amplifies the nested, or inner, segment only of *H. capsulatum*-specific DNA contained in the amplified larger DNA segment from the first amplification stage.

The first and second DNA polymerases used in the present invention are those DNA polymerases commonly employed in PCR amplification, especially DNA polymerases derived from thermophilic bacteria. The first and second DNA polymerases may be the same or different. Generally, it is preferred that the first and second DNA polymerases be the same. As those skilled in the art will realize, the first DNA polymerase may be carried over from the first PCR reaction into the second, nested PCR reaction, and may provide some or all of the second DNA polymerase in the second stage. Generally, however, it is preferred that additional DNA polymerase be added to the second stage.

The amplified DNA resulting from the second amplification is then subjected to a procedure which detects the presence of the DNA segment originating specifically from *H. capsulatum*. Several detection methods are available for this purpose. These include, by way of nonlimiting example, gel electrophoresis of the amplification product, and hybridization assays using a probe oligonucleotide, especially a probe oligonucleotide which is labeled. Gel electrophoresis resolves nucleic acids according to their size, and may be conducted, for example, in agarose gels. After electrophoresis nucleic acids are detected using a means which produces a visual image of the resolved nucleic acids in the gel, such as radioactive labeling of the DNA and exposure to film, or staining with a fluorescent dye such as ethidium bromide. It is expected to visualize a band of DNA having the size expected for the second fragment produced in the nested PCR.

Alternatively, an oligonucleotide probe may be applied to the product of the second PCR amplification to hybridize with a portion of the second fragment of *H. capsulatum* DNA. In general, such probes are labeled. Examples of probe oligonucleotides include those containing the sequences given by SEQ ID NOs:1–4, and oligonucleotides containing sequences that are complementary to those given by SEQ ID NOs:1–4.

Hybridization assays are discussed by Hall (1993). The label incorporated into the probe may be, by way of non-limiting example, radioactive labels, biotin, enzymes, digoxigenin, fluorescent probes, and chemiluminescent probes. Radioactive labels include radioactive isotopes incorporated into the structure of the probe oligonucleotide. Biotin may be incorporated into the probe by use of biotinylated nucleotides, and digoxigenin by incorporating digoxigenin-substituted nucleotides. Biotin reacts specifically with streptavidin or avidin, which itself may be conjugated to an enzyme, the enzyme acting on a substrate to produce a detectable product. Digoxigenin may bind with a digoxigenin-specific antibody which likewise may be conjugated to an enzyme. Enzyme labels may also be conjugated directly to the probe. A common way of generating chemiluminescence is via an appropriate enzyme which acts on a substrate to produce light as one product of the reaction.

When a detection method produces a result indicating that the DNA segment from the second stage of the nested PCR is present, it is concluded that the original sample contained *H. capsulatum*. Conversely, if no evidence of the DNA segment is detected after the second stage of the nested PCR, it is concluded that, within the level of detection available from the method, the sample was free of *H. capsulatum*. The present method is highly sensitive. It is estimated that this method can detect DNA from as few as 5–10 *H. capsulatum* spores or cells in a typical sample (less than about 1 mg to about 2 g). Furthermore, it is specific for *H. capsulatum* among related fungal species. Additionally, since the present method requires only about two days, it is accomplished far faster than the mouse inoculum assay, which normally requires about 6–8 weeks.

EXAMPLES

Materials

Soil samples were shown to contain *H. capsulatum* spores using the mouse inoculum assay. Clinical samples may contain *H. capsulatum* spores, or they may contain cells of the yeast form; the mouse inoculum assay may be used to establish the presence of *H. capsulatum* in clinical samples as well. *H. capsulatum* DNA was isolated from *H. capsulatum* strain G-217B. *Blastomyces dermatitidis* DNA was a generous gift from Dr. Elizabeth Keath, St. Louis Univ.

Methods.

The soil samples, and the spores, were inactivated by exposure to a temperature of 65° C. for 1 hr. The samples were then suspended in isotonic saline containing 0.01% Tween 80™. For soil, approximately 100 mg was added to about 900 µL of the saline. The sample was mixed by vigorous vortexing and allowed to settle for 30 minutes. 50 µL aliquots of the upper portion of the soil suspension were partially purified by use of Sephadex™ G-50 spin columns (4 cm×0.7 cm) containing approximately 1 ml of packed gel. Upon centrifugation the spores were found in the eluate, whereas any bulk soil remained on the surface of the column; low molecular weight contaminants were retained within the gel. This initial treatment yields partially purified preparations.

Nested PCR was carried out using methods generally described in, for example, "Current Protocols in Molecular Biology", Ausubel et al., John Wiley and Sons, New York 1987 (updated quarterly), and "Molecular Cloning: A Laboratory Manual", 2nd Ed., Sambrook, Fritsch and Maniatis, Cold Spring Harbor Laboratory, Cold Spring Harbor, N.Y., 1989. Samples were derived from purified DNA, fungal spores, or the partially purified soil extracts prepared as described in the preceding paragraph. Purified DNA, fungal spores, or partially purified soil extracts were added to a 50 µL reaction volume containing 10 mM Tris (pH 8.3), 50 mM KCl, 2.5 mM $MgCl_2$, 0.1% Triton X-100™, 5% glycerol, 8 mg/mL bovine serum albumin (BSA), 0.2 mM deoxyribonucleoside triphosphates (dNTPs), 2 units of Taq DNA polymerase, and 1 µM each of the primers ITS-1 and ITS-4 (see FIG. 1), which are considered to be generic for a broad range of fungi, and whose sequences are given respectively by:

5'-TCCGTAGGTGAACCTGCGG-3' (SEQ ID NO:1)

and

5'-TCCTCCGCTTATTGATATGC-3' (SEQ ID NO:2).

PCR was carried out using a thermal program of heating to 95° C. for 3 min., followed by 40 cycles of incubating at 95° C. for 1 min., 55° C. for 1 min., and 72° C. for 1 min.

The second round of PCR was started on a dilution of the product of the first round by between 1:200 and 1:1000. 1 µM each of the primers HC-1 and HC-2 (see FIG. 1) which were devised to be specific for *H. capsulatum*, and whose sequences are given respectively by:

5'-GGAGCCTCTGACCGGGAC-3' (SEQ ID NO:3)

and

5'-GCACGTCCCACCGGTCAG-3' (SEQ ID NO:4), were employed. The reaction mixture (50 µL) also contained 10 mM Tris (pH 8.3), 50 mM KCl, 2.5 mM MgCl$_2$, 0.2 mM dNTP's, and 2 units of Taq DNA polymerase. The reaction was carried out using a thermal cycle of heating to 95° C. for 3 min., followed by 40 cycles of incubating at 95° C. for 1 min., 60° C. for 1 min., and 72° C. for 1 min.

The amplified product of the second round was subjected to agarose gel electrophoresis using a gel concentration of 2%. Bands were detected upon staining with SyBr Green Dye (Molecular Probes, Eugene, Oreg.).

Example 1

Detection of *H. capsulatum* DNA.

This example illustrates the sensitivity and specificity of the method of the invention. Samples of purified DNA from the target organism, *H. capsulatum*, and from a related fungus, *Blastomyces dermatitidis*, were analyzed using the two-stage, or nested, PCR method of the invention. Results are shown in FIG. 2. Panel A depicts the results obtained after the first, or fungus-specific, round of PCR (i.e., using the primers given by SEQ ID NO:1 and SEQ ID NO:2). A fragment having the expected size of 600 bp is observed in samples of *H. capsulatum* DNA at levels of 100 femtogram (fg; 1 fg=$10^{-15}$ g) and 1000 fg (1 pg), but not at 50 fg (Lanes 2, 3, and 1, respectively). Samples of DNA from the related fungus, *B. dermatitidis*, (employed at concentrations of 25, 50, and 100 ng) yielded a DNA fragment of the same size (Lanes 4, 5, and 6, respectively).

The second round of PCR, using the *H. capsulatum*-specific primers (SEQ ID NO:3 and SEQ ID NO:4) gives results shown in Panel B of FIG. 1. A DNA fragment of the expected size, 400 bp, is observed for samples of *H. capsulatum* DNA that originally contained 100 fg and 1,000 fg (Lanes 8 and 9, respectively) but not for the sample originally containing 50 fg of DNA (Lane 7). The samples containing *B. dermatitidis* DNA, show no detectable DNA in this second round (Lanes 10–12) at loadings in the original samples of up to 100 ng, or one million times that of the lowest amount of *H. capsulatum* DNA that was detectable.

These results show that the nested PCR method using the primers of SEQ ID NOs: 1–4 is highly sensitive to small amounts of *H. capsulatum* DNA in a sample, while being specific for this species and not detecting the DNA of a related fungal species, even when present in vast excess. In assays in which only the second primer pair was used in a single-stage PCR amplification, the specificity and sensitivity of the assay were inadequate (not shown). These observations demonstrate that the two-stage PCR assay of the invention provides high sensitivity and specificity for the detection of *H. capsulatum* in a sample.

Example 2

Inhibition of PCR Amplification by Soil.

This example demonstrates that the presence of soil in the PCR assay medium inhibits PCR amplification. FIG. 3 shows the results of the first (fungus-specific) round of PCR for samples containing 10 ng DNA. In comparison with Lane 1, which shows an experiment with *H. capsulatum* DNA only, Lane 2 shows that a sample containing *H. capsulatum* DNA, uncontaminated soil, and 400 ng BSA in the amplification medium, and which was not subjected to purification by centrifugation through Sephadex G-50™, is inhibited from amplifying the DNA. Likewise, a sample containing soil and which was subjected to purification, but which lacked BSA in the PCR buffer, also is inhibited from amplifying DNA (Lane 4). Both purification and the presence of BSA in the PCR buffer are required to prevent inhibition of PCR amplification by the soil (Lane 3). Lanes 5 (BSA and purification) and 6 (purification only) provide positive controls for samples omitting soil from the assay. In separate experiments (not shown) the inhibitory effects of humic acid were also found to be overcome using similar techniques.

Example 3

Two-Stage PCR on Soil Samples

FIG. 4 presents results of nested PCR on soil that is free of *H. capsulatum* but spiked with *H. capsulatum* spores, and on soil samples shown to be contaminated using the indirect mouse assay (Ajello, L. and Weeks, R. J., in Occupational Mycoses, A Text, edited by A. F. DiSalvo, Leas & Febiger, Philadelphia, pp.229–238, 1983; Ajello, L. and Runyon, L. C., J. Bacteriol. 66:34–40, 1953). The uncontaminated soil was obtained from a cultivated plant bed. The contaminated soil originated from a vacant church in Manchester, Tenn. that had been subjected to evaluation for the presence of *H. capsulatum* in 1992 by the Division of Surveillance, Hazard Evaluations, and Field Studies, National Institute of Occupational Safety and Health. 100 mg of soil was employed in each assay. 1/600th of the sample solution was taken at the point of sampling to initiate PCR.

FIG. 4, Panel A shows that in the absence of soil, 10 pg of *H. capsulatum* DNA (Lane 1) and 10 *H. capsulatum* spores (Lane 2) yield the expected 400 bp band. A sample containing noncontaminated soil alone remains blank (Lane 5). Samples of soil, with 500 (Lane 4) or 1000 (Lane 3) *H. capsulatum* spores added also give positive detection of DNA. Lane 6 contains a DNA ladder of bands spaced 100 bp apart. Panel B shows samples from two batches of contaminated soil (Lanes 2–4, samples HC-13, HC-14 and HC-14, respectively). HC-13 and HC-14 were taken from different regions of the environmentally contaminated site. They yielded bands of DNA at 400 bp, as do positive controls of 1 pg *H. capsulatum* DNA (Lane 1) and 10 *H. capsulatum* spores in the absence of soil (Lane 5). A negative control is shown in Lane 6.

These experiments show that the present method using the nested primer pairs of SEQ ID NOs:1–4 permit sensitive detection of *H. capsulatum* spores in environmental soil samples.

We claim:

1. An oligonucleotide primer pair comprising sequences specific for the 5.8S rRNA gene of *Histoplasma capsulatum*, wherein both primers of said primer pair are specific for 5.8s rRNA, and wherein both primers of said pair specifically amplify 5.8S rRNA gene sequence, or an oligonucleotide comprising a sequence complementary to one or the other of the primer pair specific for the *H. capsulatum* 5.8S rRNA gene.

2. An oligonucleotide comprising a sequence given by SEQ ID NO:3 or a sequence complementary to that given by SEQ ID NO:3, wherein the sequence of SEQ ID NO:3 defines the 3' end of the oligonucleotide or wherein the sequence complementary to SEQ ID NO:3 defines the 3' end of the oligonucleotide.

3. An oligonucleotide comprising a sequence given by SEQ ID NO:4 or a sequence complementary to that given by SEQ ID NO:4, wherein the sequence of SEQ ID NO:4 defines the 3' end of the oligonucleotide or wherein the sequence complementary to SEQ ID NO:4 defines the 3' end of the oligonucleotide.

4. A method of detecting *H. capsulatum* in a sample, comprising:

(a) contacting the sample with an oligonucleotide primer pair specific for a fungal nucleic acid sequence that comprises the coding sequence for the 5.8S rRNA gene;

(b) amplifying a first amplified nucleic acid by a DNA polymerase chain reaction, wherein both primers of the oligonucleotide primer pair defines the limits of the first amplified nucleic acid and wherein the first amplified nucleic acid comprises fungal nucleic acid sequence that comprises the coding sequence for the 5.8S rRNA gene;

(c) contacting the first amplified nucleic acid from step (b) with a second oligonucleotide primer pair, wherein the second oligonucleotide primer pair are specific for the *H. capsulatum* 5.8S rRNA gene, and wherein each second oligonucleotide primer is specific for a nucleotide sequence of the first amplified nucleic acid;

(d) amplifying a second amplified nucleic acid by a DNA polymerase chain reaction, wherein the second oligonucleotide pair defines the limits of the second amplified nucleic acid; and (e) detecting an amplification product of step (d), whereby detecting the amplification product of step (d) indicates the presence of *H. capsulatum*.

5. The method of claim 4 wherein the sample is an environmental sample comprising soil or a clinical sample from a human subject.

6. The method of claim 4 wherein before step (a) the sample is subjected to partial purification comprising separation of any soil or contaminants contained in the sample from the *H. capsulatum* nucleic acid.

7. The method of claim 4 wherein the first amplified nucleic acid is amplified in a solution comprising bovine serum albumin.

8. The method of claim 4 wherein the detecting step comprises performing gel electrophoresis of the second amplified nucleic acid and detecting any *H. capsulatum*-specific DNA.

9. The method of claim 4 wherein the detecting step further comprises contacting the second amplified nucleic acid with a labeled probe specific to *H. capsulatum* DNA and detecting the label.

10. The method of claim 4 wherein the oligonucleotide primer pair employed in step (a) is specific for the fungal internal transcribed spacer regions flanking the coding sequence for the 5.8S rRNA gene.

11. The method of claim 4 wherein the sample is an environmental sample comprising soil or a clinical sample from a human subject.

12. The method of claim 4 wherein before step (a) the sample is subjected to partial purification comprising separation of any soil or contaminants contained in the sample from the *H. capsulatum* nucleic acid.

13. The method of claim 4 wherein the first amplified nucleic acid is amplified in a solution comprising bovine serum albumin.

14. The method of claim 4 wherein the detecting step (e) comprises performing gel electrophoresis of the second amplified nucleic acid and detecting any *H. capsulatum*-specific DNA.

15. The method of claim 4 wherein the detecting step (e) comprises contacting the second amplified nucleic acid with a labeled probe specific to *H. capsulatum* DNA and detecting the label.

16. The method of claim 4 wherein the detecting step (e) comprises performing gel electrophoresis of the second amplified nucleic acid and detecting any *H. capsulatum*-specific DNA.

17. The method of claim 4 wherein the detecting step (e) comprises contacting the second amplified nucleic acid with a labeled probe specific to *H. capsulatum* DNA and detecting the label.

18. A method of detecting *H. capsulatum* in a sample, comprising:
    (a) contacting the sample with a first oligonucleotide primer comprising the sequence of SEQ ID NO:1 and a second oligonucleotide primer comprising the sequence of SEQ ID NO:2;
    (b) amplifying a first amplified nucleic acid by a DNA polymerase chain reaction, wherein the first and second oligonucleotide primers define the limits of the first amplified nucleic acid;
    (c) contacting the first amplified nucleic acid from step (b) with a third oligonucleotide primer comprising the sequence of SEQ ID NO:3 and a fourth oligonucleotide comprising the sequence of SEQ ID NO:4;
    (d) amplifying a second amplified nucleic acid by a DNA polymerase chain reaction, wherein the third and fourth oligonucleotide primers define the limits of the second amplified nucleic acid; and
    (e) detecting an amplification product of step (d), whereby detecting the amplification product of step (d) indicates the presence of *H. capsulatum*.

\* \* \* \* \*